(12) United States Patent
Kurosu et al.

(10) Patent No.: US 6,375,827 B1
(45) Date of Patent: Apr. 23, 2002

(54) ELECTROCHEMICAL TREATING METHOD AND APPARATUS

(75) Inventors: Tateki Kurosu; Shuhei Wakita; Miwako Nara; Shuji Nakamatsu; Yoshinori Nishiki, all of Kanagawa (JP)

(73) Assignee: Permelec Electrode Ltd., Kanagawa (JP)

( * ) Notice: Subject to any disclaimer, the term of this patent is extended or adjusted under 35 U.S.C. 154(b) by 0 days.

(21) Appl. No.: 09/497,644

(22) Filed: Feb. 3, 2000

(30) Foreign Application Priority Data

Feb. 4, 1999 (JP) ............................................. 11-027251

(51) Int. Cl.$^7$ ................................................ C02F 1/461

(52) U.S. Cl. ........................ 205/687; 205/688; 205/746; 205/763; 205/765; 204/263; 204/265; 204/266; 204/275.1; 204/294; 204/290 F

(58) Field of Search ................................ 205/687, 688, 205/746, 763, 765; 204/263, 265, 266, 275.1, 294, 290 F

(56) References Cited

U.S. PATENT DOCUMENTS

| 5,399,247 A | * | 3/1995 | Carey et al. ................. 204/131 |
| 5,776,323 A | * | 7/1998 | Kobashi ...................... 204/294 |
| 5,900,127 A | * | 5/1999 | Iida et al. ................ 204/290 F |

* cited by examiner

Primary Examiner—Arun S. Phasge
(74) Attorney, Agent, or Firm—Sughrue Mion, PLLC

(57) ABSTRACT

An electrochemical treating apparatus comprising an electrolytic cell comprising an anode and a cathode spaced apart from the anode, the anode including an electrode material made of diamond and the cathode including an electrode material made of diamond. Also disclosed is an electrochemical treating method for electrochemically decomposing a substance contained in a gas or solution, which comprises introducing a gas or solution containing a substance to be treated into the electrolytic cell, passing an electric current through the electrolytic cell, and recovering a treated gas or solution. In a preferred embodiment, the electrolytic cell comprises an anode including an electrode material made of diamond, a cathode including an electrode material made of diamond and an ion exchange resin or an ion exchange membrane as an electrolyte disposed between the anode and the cathode.

22 Claims, 5 Drawing Sheets

ELECTROCHEMICAL TREATING METHOD AND APPARATUS

FIELD OF THE INVENTION

The present invention relates to an electrochemical method and apparatus for electrochemically treating a solution or gas containing impurities or environmental pollutants, such as environmental hormones, to decompose the impurities into harmless low molecular weight compounds.

BACKGROUND OF THE INVENTION

It has recently been recognized that atmospheric pollution and deterioration of the quality of water in rivers, lakes and marshes arising from industrial and livelihood wastes have adverse effects on the environment and human body. Thus, there is an urgent need to develop technical countermeasures against these problems. In the treatment of drinking water and the disposal of sewage and waste water, for example, chemicals such as chlorine have been added to decolor the water, lower COD or sterilize the water. However, the use of chlorine causes the production of new dangerous materials, namely, environmental hormones (exogenous secretion disturbing materials) and carcinogens. Thus, the use of chloride tends to be prohibited. In the incineration of wastes, carcinogen (dioxin) can be produced in the waste gas under some combustion conditions. Therefore, the safety of incineration has been questioned. In order to solve these problems, new methods have been studied.

In the electrolysis method, electric energy, which is a clean energy, is used to control chemical reaction on the surface of electrodes, thereby producing hydrogen, oxygen, ozone, hydrogen peroxide, etc. A substance to be treated can then be indirectly decomposed by these products. Alternatively, the substance to be treated can be adsorbed by the electrodes where it is then directly electrolyzed. Such an electrolysis has heretofore been employed to dispose of waste water. It is desirable that the decomposition products eventually become low molecular and safe materials such as carbon dioxide, water, hydrogen, oxygen, nitrogen, ammonia and chloride ion. However, it is known that some intermediate products in the course of decomposition are rather dangerous.

Extensive studies of electrodes and reactants are disclosed in "Denki Kagaku", vol. 62, pp. 1,084-(1992), "Journal of Applied Electrochemistry", vol. 21, pp. 99–104 (1991), etc. It is pointed out that substances to be treated cannot be sufficiently decomposed depending on the performance of electrodes. In general, anodization reaction by electrolysis of an aqueous solution results in the production of an electrolysis product with water as a starting material. In most cases, the oxidation of other ingredients cannot easily proceed in the presence of an electrode catalyst having a high reactivity with respect to the electric discharge of water.

Examples of electrode materials which perform oxidation include lead oxide, tin oxide, platinum, DSA and carbon. Examples of electrode materials which perform reduction include lead, iron, platinum, titanium and carbon. The material employable as an electrode substrate needs to be corrosion-resistant to prolong the cell life and prevent stain on the surface to be treated. The anodic power supplying material is limited to valve metals such as titanium and alloys thereof. The electrode catalyst is limited to noble metals such as platinum and iridium and oxides thereof. However, it is known that even these expensive materials, if used, are consumed and eluted with the electrolytic solution depending on the current density or time over which the cell is energized. It has thus been desired to provide electrodes having better corrosion resistance.

Graphite and amorphous carbon material have heretofore been used as electrode materials, but leave something to be desired in consumption resistance. In particular, these materials can be heavily consumed during positive polarization. Diamond is excellent in thermal conductivity, optical transmission and durability against heat and oxidation. In particular, The thermal conductivity of diamond can be controlled when properly doped with additives. Therefore, diamond has been favorably considered as semiconductor devices and energy conversion elements. Swain et al. reported the stability of diamond as an electrochemical electrode in an acidic electrolytic solution in "Journal of Electrochemical Society", vol. 141, pp. 3,382-(1994) and thus suggested that diamond is far superior to other carbon materials. Focusing on the magnitude of the band gap (4.5 V) of diamond, Fujishima et al. reported in "Journal of Electroanalytical Chemistry", vol. 396, pp. 233-(1995) and "Denki Kagaku", vol. 60, No. 7, pp. 659-(1992) that NOx can be reduced to ammonia using diamond. Some reports disclose a humidity sensor that makes the use of the change in surface resistivity of diamond with humidity ["Denkiron", vol. 114, No. 5, pp. 413-(1994)]. U.S. Pat. No. 5,399,247 suggests that the use of diamond as an anode material makes it possible to decompose an organic waste water.

Although sufficient reports have never been made on the industrial use of diamond electrodes at a high current density in a high potential range, it has recently been reported that diamond electrode is inert to the decomposition reaction of water and produces ozone and hydrogen peroxide besides oxygen in the oxidation reaction [Japanese Journal of Applied Physics, vol. 36, L260-, (1997)]. Hydrogen peroxide and ozone are materials from which OH radicals having a higher oxidizing power are produced. It is known that radicals can be easily produced in the presence of hydrogen peroxide or ozone. Accordingly, it is expected that the use of diamond as an electrode makes it possible to provide enhanced efficiency over systems using conventional electrodes. From a practical standpoint, improvements have been desired for further enhancement of cell efficiency.

SUMMARY OF THE INVENTION

It is therefore an object of the present invention to provide a method and apparatus which can attain further enhanced efficiency in electrochemical treating involving the decomposition of substances in waste water or the like using diamond as an electrode material.

The foregoing object of the present invention will become apparent from the following detailed description and examples.

The above objects of the present invention have been achieved by providing an electrochemical treating apparatus comprising an electrolytic cell comprising an anode and a cathode spaced apart from said anode, the anode including an electrode material made of diamond and the cathode including an electrode material made of diamond. The above objects of the present invention have also been achieved by providing an electrochemical treating method for electrochemically decomposing a substance contained in a gas or solution, which comprises introducing a gas or solution containing a substance to be treated into an electrolytic cell comprising an anode and a cathode spaced apart from said anode, said anode including an electrode material made of diamond and said cathode including an electrode material made of diamond, passing an electric current through the electrolytic cell, and recovering a treated gas or solution. In a preferred embodiment, the electrolytic cell comprises an anode including an electrode material made of diamond, a cathode including an electrode material made of diamond and an ion exchange resin or an ion exchange membrane as an electrolyte disposed between the anode and the cathode. A gas or solution containing a substance to be treated is contacted with the anode and cathode to decompose the substance into lower molecular weight components. Alternatively, a gas or solution containing a substance to be treated is contacted with the anode and cathode so as to generate oxidizing and/or reducing species which in turn act to decompose the substance into lower molecular weight components.

BRIEF DESCRIPTION OF THE DRAWINGS

By way of example and to make the description more clear, reference is made to the accompanying drawings in which.

Figure 1:
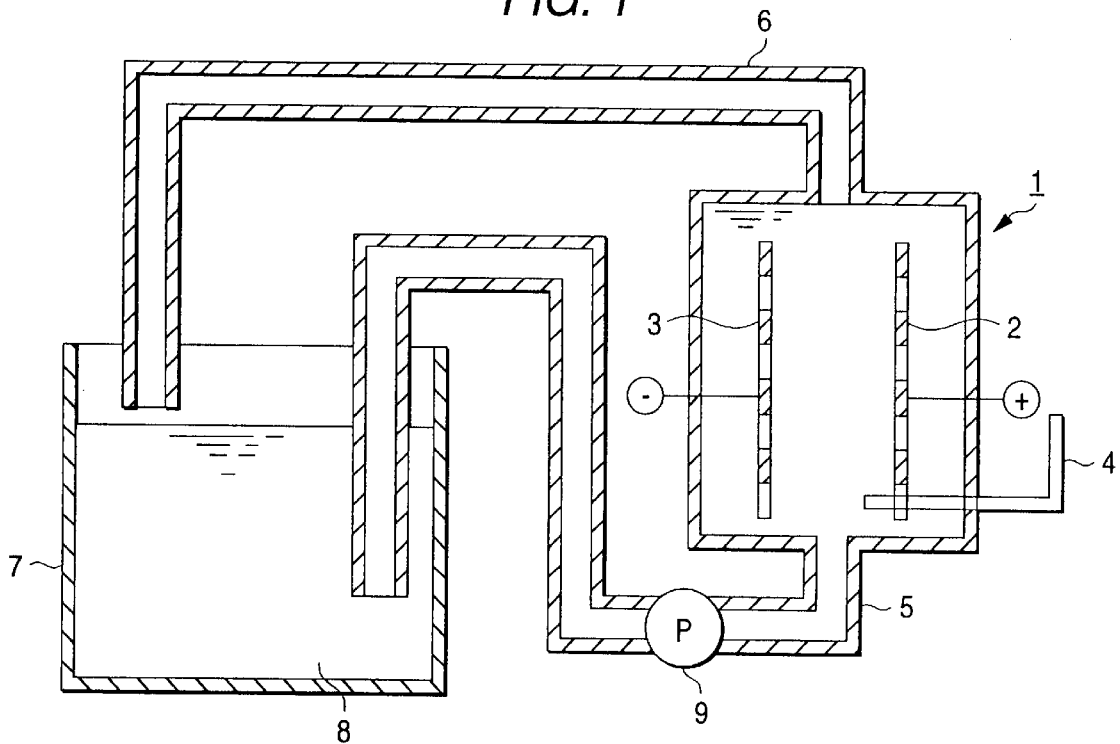
FIG. 1 is a schematic vertical section illustrating an embodiment of the electrochemical treating apparatus according to the invention.

In the drawings, the reference numeral 1 indicates an electrolytic cell, the reference numeral 2 indicates an anode, the reference numeral 3 indicates a cathode, the reference numeral 4 indicates a reference electrode, the reference numeral 5 indicate a water supply pipe, the reference numeral 6 indicates a circulating pipe, the reference numeral 7 indicates a stock solution tank, the reference numeral 8 indicates an aqueous solution, the reference numeral 9 indicates a pump, the reference numeral 10 indicates an electrolytic cell, the reference numeral 11 indicates an ion exchange membrane, and the reference numeral 12 indicates an electrode structure.

DETAILED DESCRIPTION OF THE INVENTION

The present invention will be further described hereinafter.

In general, ordinary anodization reactions in an electrolytic cell containing water proceed with water as a starting material in accordance with the following reaction formulae to give an electrolysis product. The oxidation of other ingredients can easily proceed on an electrode catalyst which is less reactive than water to be electrolyzed.

Anode:
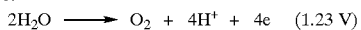
$2H_2O \longrightarrow O_2 + 4H^+ + 4e$ (1.23 V)
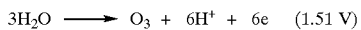
$3H_2O \longrightarrow O_3 + 6H^+ + 6e$ (1.51 V)
$2H_2O \longrightarrow H_2O_2 + 2H^+ + 2e$ (1.78 V)

The main reaction on the anode with an aqueous solution containing chloride ion proceeds in accordance with the following formula:

$$2Cl^- \rightarrow Cl_2 + 2e \qquad (1.36\ V)$$

The resulting chlorine gas is dissolved in and then, depending on the pH, reacts with water to produce hypochlorous acid.

These reactions can take place also on an anode made of diamond as an electrode material but require a large overvoltage. It is thought that water is oxidized on the surface of diamond as an anode material to form thereon oxygen chemical species which then produce oxygen or ozone. However, the chemical stability of diamond makes it difficult to oxidize water molecules. Thus, the amount of oxidized water is very small. On the other hand, an organic material having a great affinity for carbon (most materials to be treated are organic materials) can easily be adsorbed by the diamond surface. Thus, an organic material easily undergoes direct oxidation in a range where oxidation can potentially proceed. In other words, the material to be treated contacts the surface of the electrode on which it is then oxidatively decomposed. Besides these reactions, indirect oxidative decomposition takes place by the foregoing oxygen chemical species, namely, ozone, hydrogen peroxide, hypochlorous acid and radicals arising therefrom.

On the other hand, the reduction reaction on a cathode with water as a starting material proceeds in accordance with the following reaction formulae:

Cathode:
$2H^+ + 2e \longrightarrow H_2$ 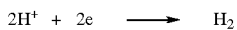
$2H_2O + 2e \longrightarrow H_2 + 2OH^-$ 

When oxygen is supplied to the cathode, the following reaction takes place:

Cathode: $2O_2 + 4H^+ + 4e \rightarrow 4OH^- + HO_2^-$ 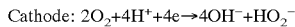

Under some reaction conditions, dielectronic reduction or monoelectronic reduction may take place to produce hydrogen peroxide or superoxide anion ($O^{2-}$).

These reactions can take place also on the cathode made of diamond as an electrode material. However, these reactions require a large overvoltage. It is thought that water is adsorbed and reduced by the surface of diamond as a cathode material to produce hydrogen. However, since diamond is a p-type material, the reduction reaction by positive hole carriers is limited. Further, the chemical stability of diamond makes it difficult for water molecules to be reduced. Thus, the amount of reduced water molecules is very small. A surface state developed by adsorbed hydrogen atom or impurities then exists. The reaction proceeds via this surface state. An organic material having a great affinity for carbon can be easily adsorbed by the surface of diamond. Thus, an organic material readily undergoes direct reduction in a range where reduction can potentially proceed. Further, indirect reduction decomposition by the resulting hydrogen takes place.

Both the foregoing anodization and cathodic reduction are single reactions and thus are unsuitable for the treatment of materials which are relatively difficult to decompose.

The present invention is characterized in the use of diamond as both anode and cathode materials instead of the conventional method involving the use of diamond as either an anode or cathode material. The present invention allows efficient electrolysis of substances contained in waste water and waste gas which impart adverse effects on the human body and environment.

Diamond, which is an electrode material of the invention, may be applied in the form of a powder to the surface of a plate, punched plate, gauze, sintered powder or sintered fiber of titanium, niobium, tantalum, silicon, carbon, nickel or tungsten carbide as a substrate by the method described below. Alternatively, tabular diamond may be used as an electrode as is. From an economical standpoint, the former arrangement is preferred. For the purpose of providing improved adhesivity and protecting the substrate, an interlayer is preferably formed. The material of the interlayer may be a carbide or oxide of the metal constituting the foregoing substrate. The surface of the substrate is preferably polished to further increase adhesivity and reaction area. The substrate may comprise a small amount of other electrode materials incorporated therein besides diamond. The foregoing substrate also acts as a diamond collector. In the case where a diamond plate is used, another collector may be prepared to supply electric power to the diamond electrode.

Methods for forming a diamond layer on the surface of the substrate include a hot filament CVD method, a microwave plasma CVD method, a plasma arc jet method, a PVD method, etc.

The hot filament CVD method, which is a representative method for forming a diamond layer, will be described hereinafter. In some detail, an organic compound which acts as a carbon source such as an alcohol is kept at a temperature range of from 1,800° C. to 2,400° C., where carbon radicals are produced, in a reducing atmosphere such as hydrogen gas. During this procedure, the electrode substrate is disposed in a temperature range where diamond is deposited (750° C. to 950° C.). The concentration of the organic compound gas with respect to hydrogen is preferably from 0.1 to 10% by volume. The supply rate of the organic compound gas is preferably from 0.01 to 10 l/min, depending on the dimension of the reaction vessel. The pressure of the organic compound gas is from 15 to 760 mmHg. The particulate diamond normally has a particle diameter of from about 0.01 to 1 $\mu$m. In the present invention, diamond powder is vacuum-evaporated onto the foregoing substrate under the foregoing conditions to form a diamond layer having a thickness of from 0.1 to 50 $\mu$m, preferably from 1 to 10 $\mu$m. This thickness is suitable for preventing the penetration of electrolyte into the substrate. In order to impart good electrical conductivity to the resulting diamond layer, elements having different valences are necessarily incorporated into the diamond layer in a slight amount. For example, phosphorus or boron may be incorporated into the diamond layer in an amount of from 1 to 100,000 ppm, preferably from 100 to 10,000 ppm. The compound to be added is preferably boron pentaoxide or biphosphorus pentaoxide, which is slightly toxic.

In the present invention, diamond powder synthesized under an ultrahigh pressure may be used instead of diamond prepared by vacuum evaporation or the foregoing natural diamond. Such a synthetic diamond powder can be bonded to the substrate with a binder such as a resin. In particular, the use of a hydrophobic component such as a fluororesin makes it easy to trap the substance to be treated, making it possible to enhance the reaction efficiency. Alternatively, DLN (diamond like nano-composite), which is a composite with amorphous silicon oxide, may be used in the present invention.

The electrolysis conditions are not particularly limited. In practice, however, current density is preferably from 0.01 to 10 A/dm$^2$ and the electrolysis temperature is preferably from 5 to 40° C. The material constituting the electrolytic cell is preferably a glass-lined material, carbon or titanium, stainless steel or PTFE resin, which has excellent corrosion resistance, from the standpoint of durability and stability of hydrogen peroxide thus produced.

Because the electrolyte or gas containing a substance to be treated is desirably supplied to the electrolysis surface at a sufficient rate, the solution or gas is preferably stirred between the electrodes.

In the case where a solution or gas having a low electrical conductivity is treated, an ion exchange membrane or ion exchange resin is preferably used as an electrolyte. The ion exchange membrane, if used, may be either fluororesin-based or hydrocarbon resin-based. In practice, however, the former is preferred from the standpoint of corrosion resistance. NAFION (Du Pont), ACIPLEX (ASAHI CHEMICAL INDUSTRY CO., LTD.), FLEMION (Asahi Glass Co., Ltd.), etc., are commercially available ion exchange membranes for use in the present invention. This ion exchange membrane is capable of enhancing the electrical conductivity of an electrolytic solution or gas having a low electrical conductivity to facilitate electrolysis. Although this ion exchange membrane does not basically act as a partition by which the two electrode chambers are separated from each other as in the ordinary electrolysis of brine, it may be used to prevent various ions produced on the anode and cathode from being consumed on the respective opposing electrodes.

The foregoing ion exchange membrane or resin is preferably used in close contact with the anode and the cathode. To this end, these members may be previously bonded mechanically to each other. Alternatively, the ion exchange membrane, if used, may be pressed at 0.1 to 30 kgf/cm$^2$ during electrolysis.

Further, in the present invention, diamond may be applied to particles of carbon or the like to give coated particles which are then used as tertiary electrodes (fluidized bed or fixed bed). In this arrangement, the reaction area can be considerably increased, making it possible to enhance the treating capacity.

In accordance with the method of the invention, a solution containing a substance to be treated is used as an electrolytic solution. The solution is contacted with the anode or cathode made of diamond as an electrode material so that a substance to be treated such as a contaminant is directly or indirectly decomposed to low molecular compounds which are low burden to the environment. Examples thereof include a method of disposing diamond plates or diamond-coated substrates as an anode and a cathode apart from each other in an electrolytic cell and a method using diamond-coated particles as a tertiary electrode which is energized through the power supply electrodes.

In the apparatus of the invention, an ion exchange membrane or ion exchange resin is interposed between an anode and cathode each made of diamond as an electrode material. In this arrangement, a solution or gas containing a substance to be treated is allowed to penetrate into the ion exchange resin or membrane. The substance to be treated then contacts the diamond so that the substance to be treated such as a contaminant is directly or indirectly decomposed to low molecular compounds which are a low burden to the environment.

Most of the main substances to be treated such as environmental hormones and carcinogens are hydrophobic organic materials having a high affinity for the living body. Accordingly, it is considered that the use of diamond as an anode and cathode material makes it easy for a part of the substance to be treated to undergo oxidation causing decomposition or structural change on the anode. This is followed by easy reduction on the cathode while making it easy for another part of the substance to undergo reduction causing structural change or decomposition on the cathode followed by easy oxidation on the anode, thereby providing a synergistic effect.

Figure 2:
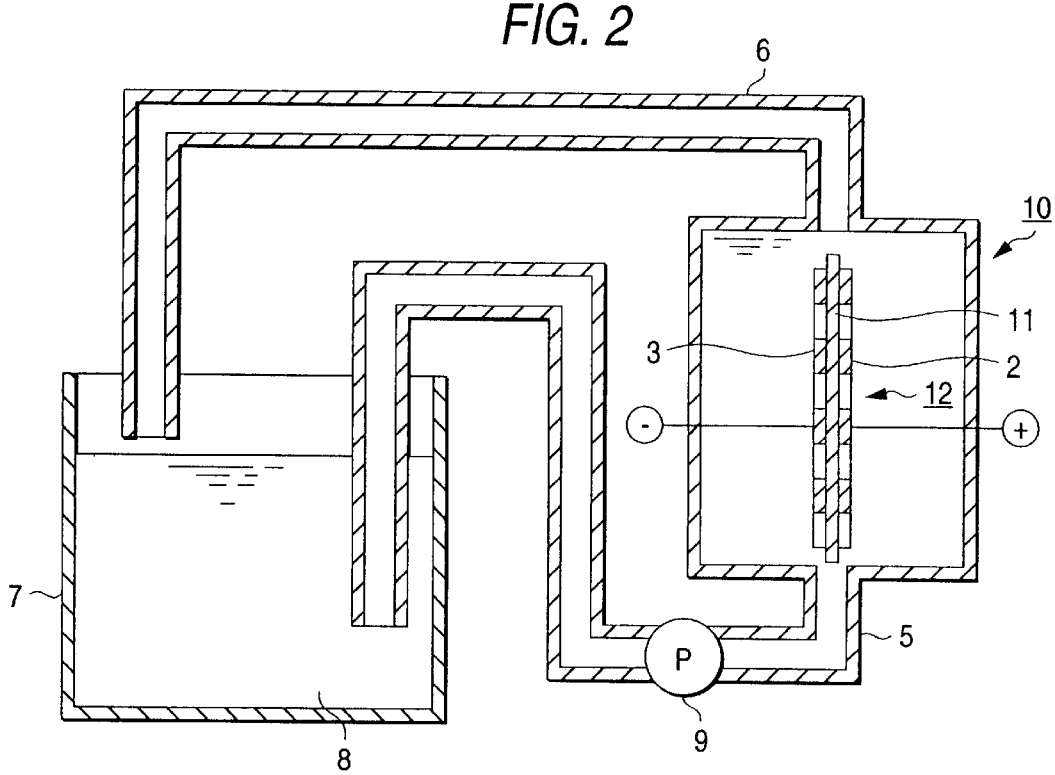
FIG. 2 is a schematic vertical section illustrating another embodiment of the electrochemical treating apparatus according to the invention.

FIGS. 1 and 2 each indicate an example of an electrolytic cell for use in the present invention. FIG. 1 is a diagram illustrating an electrolytic cell comprising an anode and a cathode disposed apart from each other. FIG. 2 is a diagram illustrating an electrolytic cell comprising an ion exchange membrane as an electrolyte.

In FIG. 1, a box-shaped electrolytic cell 1 comprises an anode 2 and a cathode 3 each coated with powdered diamond on the surface thereof disposed apart from each other inside the electrolytic cell. Disposed in the space between the two electrodes is the forward end of a reference electrode 4 such as a mercurous sulfate reference electrode for detecting the potential to confirm performance. The electrolytic cell 1 is connected to a stock solution tank 7 through a water supply pipe 5 and a circulating pipe 6. In this arrangement, an aqueous solution 8 containing a substance to be treated in the stock solution tank 7 is pumped by a pump 9 into the electrolytic cell 1 at the bottom thereof through the water supply pipe 5. The substance to be treated in the solution thus supplied then comes into contact with the anode 2 and the cathode 3 where it is directly decomposed and/or indirectly decomposed by oxidizing or reducing materials produced by the electrolysis of water. The solution thus treated is then returned to the stock solution tank 7 through the circulation pipe 6, which runs from the top of the electrolytic cell 1. When the ingredients contained in the solution thus returned are found to have undergone insufficient decomposition, the solution is then again supplied to the electrolytic cell 1 through the water supply pipe 5 for retreating.

The electrolytic cell of FIG. 2 concerns an improvement in the electrolytic cell of FIG. 1. Where the parts are the same as those of FIG. 1, the same numbers are used and their description is omitted.

In FIG. 2, an electrolytic cell 10 comprises an electrode structure 12 disposed thereinside, the electrode structure having the same anode 2 and cathode 3 as used in FIG. 1 provided in close contact with the respective sides of a fluororesin-based cation exchange membrane 11 which serves as an electrolyte. The foregoing ion exchange membrane 11 is not capable of defining the anode chamber and the cathode chamber and thus does not need to be disposed in contact with an inner wall of the electrolytic cell 10.

The electrolytic cell of FIG. 1 is disadvantageous in that if the aqueous solution containing a substance to be treated has a low electrical conductivity, sufficient current cannot flow when the two electrodes are energized, possibly causing the substance to be returned undecomposed to the stock solution tank 7. On the contrary, in the electrolytic cell of FIG. 2, the aqueous solution which has been supplied to the electrolytic cell 10 is absorbed by an ion exchange membrane 11 which has become wet. Since the ion exchange membrane 11 contains sulfonic acid groups or carboxylic acid groups and thus has good conductivity, the substance to be treated can be sufficiently decomposed in the ion exchange membrane 11. Unlike the electrolytic cell of FIG. 1, which can hardly decompose a gaseous material, the electrolytic cell of FIG. 2 can decompose a gaseous material at a sufficiently high efficiency because the two electrodes can be sufficiently energized and the substance to be treated resides in the ion exchange member 11 for a period of time.

The present invention will be further described in the following examples of decomposition of a substance to be treated by the electrochemical treating method according to the invention. While amaranth, which is a starting material of red dye, is used as a substance to be treated in the following examples, the present invention should not be construed as being limited thereto because the method according to the invention allows the decomposition of many compounds such as environmental hormones and pesticides. Further, other descriptions in the following examples should not be construed as limiting the invention.

EXAMPLE 1

A diamond layer (B/C: 10,000 ppm (B/C represents the atomic ratio of boron in carbon) corresponding to 1 atm %) was deposited on a metal titanium plate having an electrode area of 1 cm$^2$ (1 cm×1 cm) and a thickness of 1 mm to a thickness of 3 $\mu$m by a hot filament CVD method to form an anode. Similarly, a cathode having a diamond layer having a B/C ratio of 1,000 ppm deposited thereon to a thickness of 3 $\mu$m was prepared. The anode and the cathode were then disposed apart from each other at a distance of 3 mm with a mercurous sulfate electrode mounted as a reference electrode to assemble the electrolytic cell shown in FIG. 1.

Figure 3:
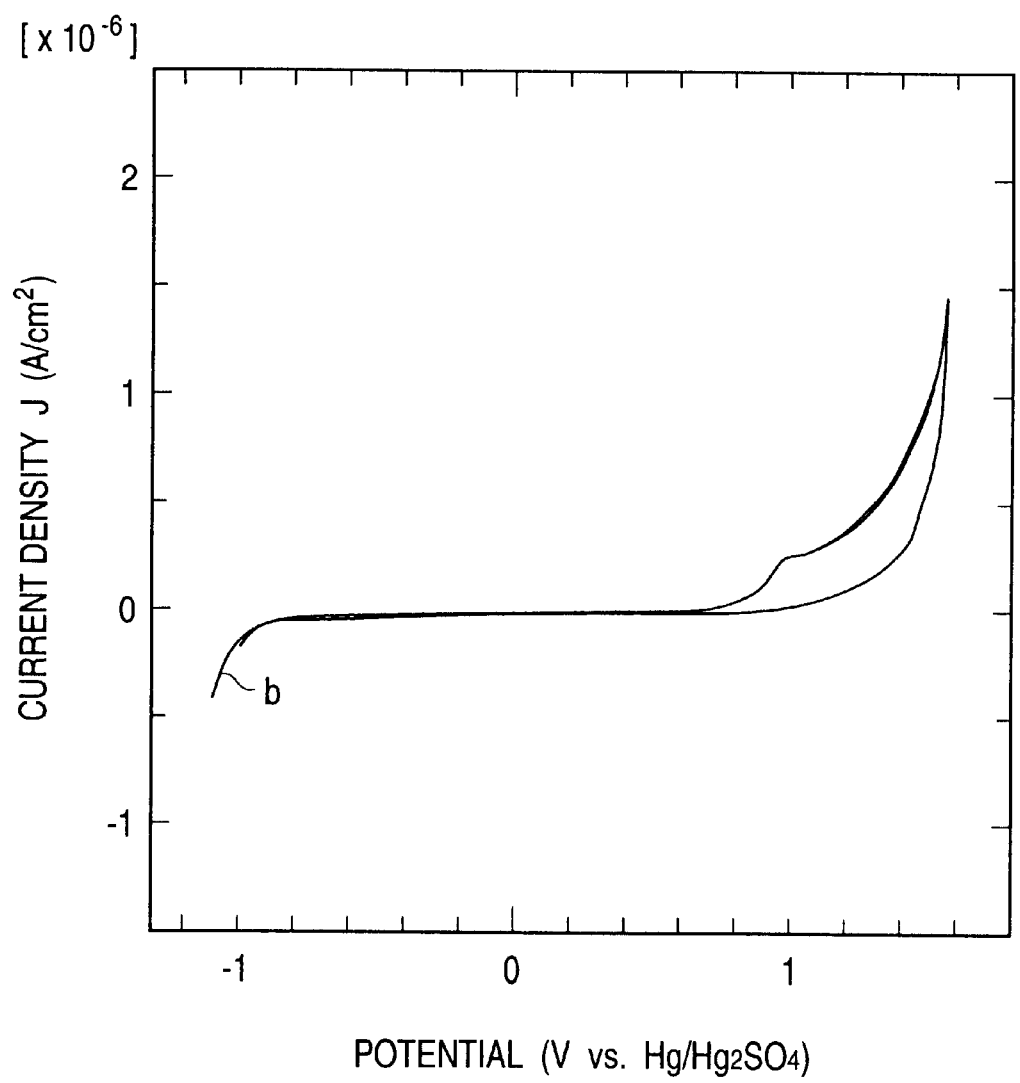
FIG. 3 is a graph illustrating the potential-current curve of diamond electrode in an aqueous solution of sulfuric acid of Example 1.

The electrolytic cell thus assembled was then energized while being supplied with an aqueous solution of sulfuric acid having a concentration of 150 g/l. Using the foregoing reference electrode, the relationship between the initial potential of the diamond electrode and the current density was measured. As a result, a potential-current curve as shown in FIG. 3 was obtained. Subsequently, the electrolytic cell was energized while being supplied with a 150 g/l aqueous solution of sulfuric acid containing 100 ppm of amaranth instead of the foregoing 150 g/l aqueous solution of sulfuric acid. The relationship between the initial potential of the diamond electrode and the current density was measured. As a result, a potential-current curve as shown in FIG. 4 was obtained.

Figure 4:
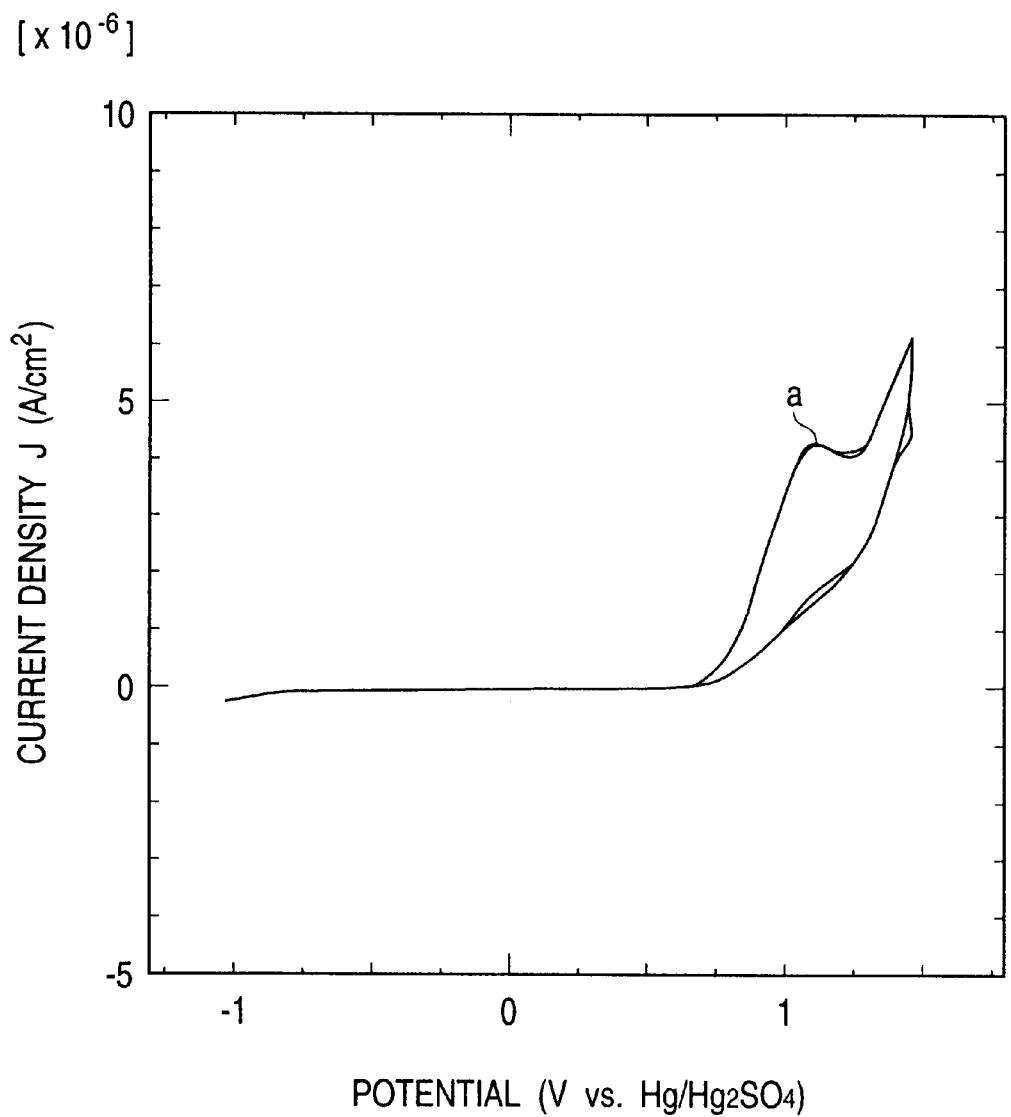
FIG. 4 is a graph illustrating the potential-current curve of diamond electrode in an aqueous solution of sulfuric acid containing amaranth of Example 1.

The comparison of FIGS. 3 and 4 gives the following results. Namely, the increase in oxidation current in the vicinity of 1 V potential in FIG. 4 (peak (a)) corresponds to the partial oxidation of amaranth.

EXAMPLE 2

Figure 5:
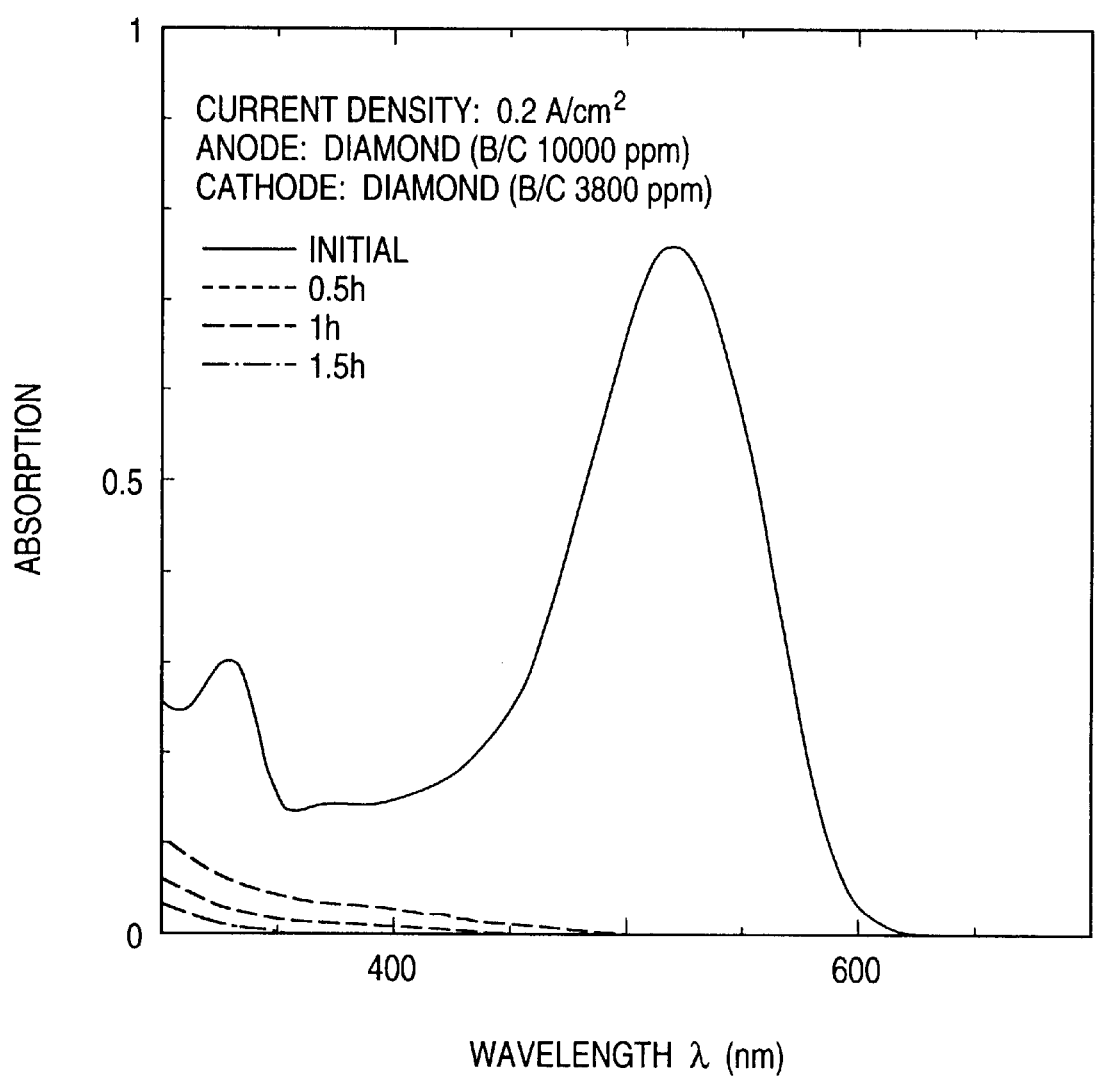
FIG. 5 is a graph illustrating the absorption spectrum of an aqueous solution of sodium sulfate containing amaranth of Example 2.

The same electrolytic cell as in Example 1 was used. The electrolytic cell was energized at a current of 0.2 A and a temperature of 20° C. with a 10 g/l aqueous solution of sodium sulfate containing 100 ppm of amaranth being circulated at a rate of 10 cc per minute (initial COD value: 70 ppm) so as to decompose amaranth. As a result, the cell voltage remained almost constant (5 V). The absorption spectrum in the vicinity of 520 nm based on which the change in amaranth concentration at the outlet of the electrolytic cell at the initial stage and after 0.5 hours, 1 hour and 1.5 hours was calculated is shown in FIG. 5. FIG. 5 shows that the concentration of amaranth falls with time. After 2 hours, the aqueous solution was almost decolored, and COD was reduced to 1 ppm. The resulting decomposition product was then analyzed. As a result, low molecular compounds ($CO_3^-$, oxalic acid, etc.) were found to be produced as the decomposition product of amaranth.

Comparative Example 1

Figure 6:
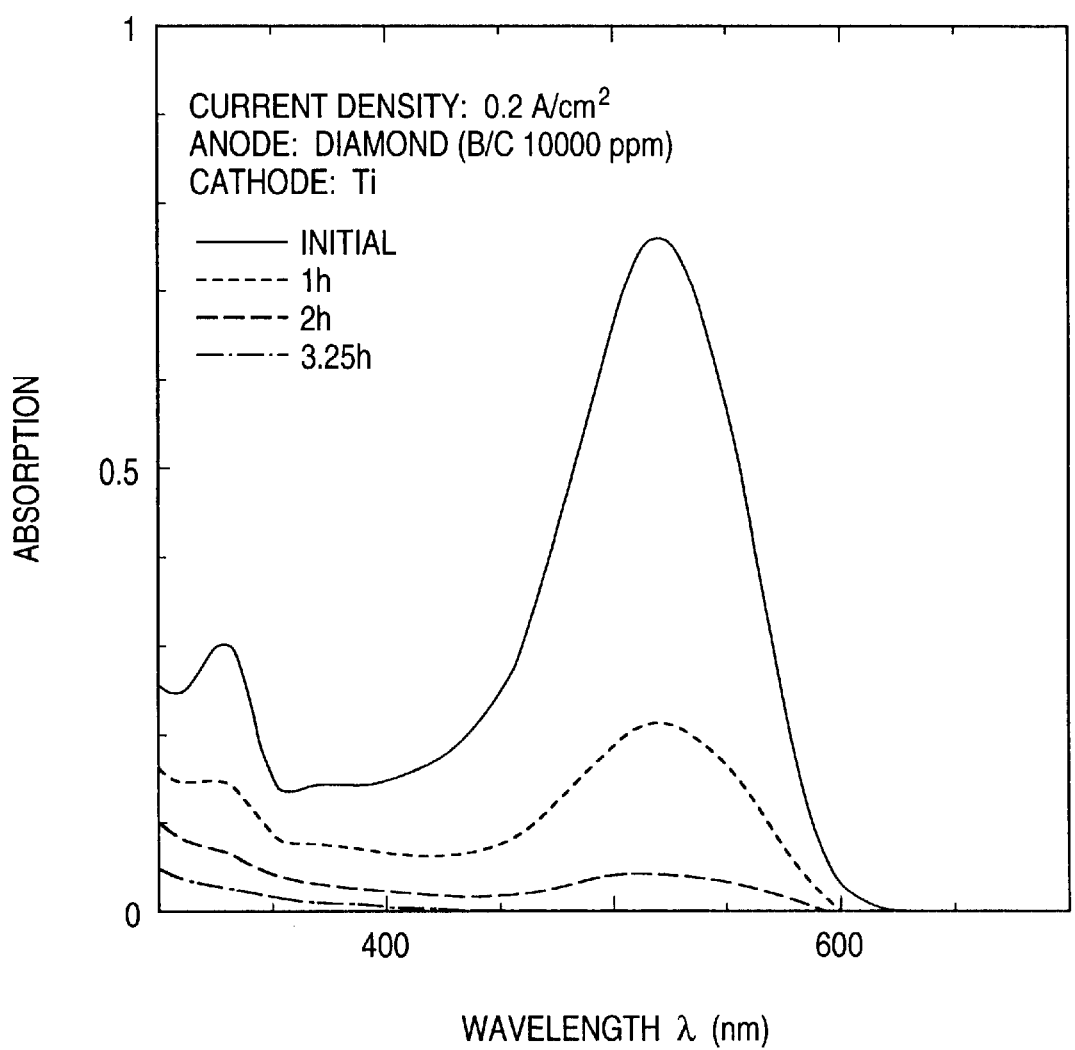
FIG. 6 is a graph illustrating the absorption spectrum of an aqueous solution of sodium sulfate containing amaranth of comparative Example 1.

The same evaluation as in Example 1 was carried out using the same electrolytic cell as in Example 1, except that a titanium plate having an electrode area of 1 $cm^2$ was used as the cathode. The concentration of amaranth at the outlet of the electrolytic cell showed a change with time (see the absorption spectrum of FIG. 6 indicating the concentration of amaranth at the outlet of the electrolytic cell at the initial stage and after 1 hour, 2 hours and 3.25 hours). However, it took 7 hours until almost all of the amaranth was decolored. At that time, the COD was 5 ppm. The resulting decomposition product was analyzed. As a result, low molecular compounds were found to be produced as the decomposition product of amaranth.

Comparative Example 2

The same evaluation as in Example 1 was carried out using the same electrolytic cell as in Example 1, except that a glassy carbon plate having an electrode area of 1 $cm^2$ was used as a cathode. The concentration of amaranth at the outlet of the electrolytic cell showed a change with time. However, amaranth was hardly decomposed and was found remaining in the aqueous solution of sulfuric acid after 2 hours. After treatment for 2 hours, the COD was 40 ppm. The resulting decomposition product was analyzed. As a result, low molecular compounds were found to be produced as the decomposition product of amaranth.

Comparative Example 3

The same evaluation as in Example 1 was carried out using the same electrolytic cell as in Example 1, except that a platinum plate having an electrode area of 1 $cm^2$ was used as the anode, and a titanium plate having an electrode area of 1 $cm^2$ was used as the cathode. The concentration of amaranth at the outlet of the electrolytic cell showed a change with time. However, amaranth was hardly decomposed and was found remaining in the aqueous solution of sulfuric acid after 2 hours. After treatment for 2 hours, the COD was 40 ppm.

Comparative Example 4

The same evaluation as in Example 1 was carried out using the same electrolytic cell as in Example 1, except that a platinum plate having an electrode area of 1 $cm^2$ was used as the anode, and a diamond plate having an electrode area of 1 $cm^2$ was used as the cathode. The concentration of amaranth at the outlet of the electrolytic cell showed a change with time. However, amaranth was hardly decomposed and was found remaining in the aqueous solution of sulfuric acid after 2 hours. After treatment for 2 hours, the COD was 40 ppm.

EXAMPLE 3

A diamond layer (B/C: 4,000 ppm) was deposited on a porous metal plate of titanium having a thickness of 3 mm to a thickness of 2 $\mu$m by a microwave plasma CVD method to prepare an anode and a cathode each having an electrode area of 5 $cm^2$. The anode and the cathode thus prepared were then disposed in close contact with the respective sides of a NAFION 117 cation exchange membrane available from Du Pont to form an electrolytic cell as shown in FIG. 2. The electrolytic cell thus formed was then energized with a current of 0.25 A at a temperature of 20° C. with pure water containing 100 ppm of amaranth (initial COD: 70 ppm) being supplied at a rate of 10 cc per minute. As a result, the cell voltage remained almost constant (4 V). The concentration of amaranth at the outlet of the electrolytic cell showed a change with time. After 2 hours, the aqueous solution was almost decolored, and COD was reduced to 1 ppm. The resulting decomposition product was then analyzed. As a result, low molecular compounds ($CO_3^-$, oxalic acid, etc.) were found to be produced as the decomposition product of amaranth.

The present invention concerns an electrochemical treating method for electrochemically decomposing a substance to a low molecular compound, characterized in that the anode material and the cathode material comprise diamond. Examples of the method of the invention include a method of disposing the two electrodes apart from each other and a method of using an ion exchange membrane or resin as an electrolyte with which the two electrodes are provided in close contact.

Unlike conventional treating methods where diamond is incorporated as either one of the two electrode materials, the method of the invention allows the use of both anodization and cathode reduction for the decomposition of the substance to be treated, providing a synergistic effect that considerably enhances the decomposition effect.

Further, the use of an electrochemical treating apparatus according to the invention comprising an ion exchange resin or ion exchange membrane as an electrolyte interposed between an anode made of diamond as an anode material and a cathode made of diamond as a cathode material, whereby a gas or solution containing a substance to be treated is contacted with the anode and cathode and/or the resulting oxidizing or reducing material decomposes said substance to a low molecular compound, makes it possible to decompose such substance in an aqueous solution or gas having a low conductivity. Substances contained in an aqueous solution or gas having a low conductivity cannot be decomposed by a conventional electrolytic cell comprising two electrodes disposed apart from each other.

While the invention has been described in detail and with reference to specific embodiments thereof, it will be apparent to one skilled in the art that various changes and modifications can be made therein without departing from the spirit and scope thereof.

What is claimed is:

1. An electrochemical treating apparatus comprising an electrolytic cell including a reaction chamber and an anode and a cathode spaced apart from said anode, said anode and cathode being arranged within the same reaction chamber, said anode including an electrode material made of diamond and said cathode including an electrode material made of diamond.

2. The electrochemical treating apparatus as claimed in claim 1, said electrolytic cell further comprising an inlet for supplying a gas or solution containing a substance to be treated and an outlet for removing a treated gas or solution.

3. The electrochemical treating apparatus as claimed in claim 2, further including a stirrer for increasing the rate of supply of the gas or solution to be treated to the electrode materials of the anode and cathode, respectively.

4. The electrochemical treating apparatus as claimed in claim 1, wherein at least one of said and anode and cathode comprises a substrate having a surface and a diamond layer formed on the surface of the substrate.

5. The electrochemical treating apparatus as claimed in claim 4, wherein said substrate is selected from the group consisting of a punched plate, gauze, sintered powder or sintered fiber of titanium, niobium, tantalum, silicon, carbon, nickel or tungsten carbide.

6. The electrochemical treating apparatus as claimed in claim 4, wherein the diamond layer has a thickness of from 0.1 to 50 µm.

7. The electrochemical treating apparatus as claimed in claim 4, wherein said diamond is bonded to the substrate with a binder.

8. The electrochemical treating apparatus as claimed in claim 1, wherein the diamond contains an impurity for imparting electrical conductivity to said anode and cathode electrode materials.

9. An electrochemical treating apparatus comprising an electrolytic cell comprising an anode including an electrode material made of diamond, a cathode including an electrode material made of diamond and an ion exchange resin or an ion exchange membrane as an electrolyte disposed between said anode and said cathode.

10. The electrochemical treating apparatus as claimed in claim 9, wherein said electrolyte comprises an ion exchange membrane and said anode and cathode are in close contact with opposing sides of said ion exchange membrane.

11. The electrochemical treating apparatus as claimed in claim 9, wherein said electrolyte comprises an ion exchange resin and said anode and cathode are in close contact with said ion exchange resin.

12. The electrochemical treating apparatus as claimed in claim 9, wherein at least one of said anode and cathode comprises a substrate having a surface and a diamond layer formed on the surface of the substrate.

13. The electrochemical treating apparatus as claimed in claim 12, wherein the diamond layer has a thickness of from 0.1 to 50 µm.

14. The electrochemical treating apparatus as claimed in claim 9, wherein the diamond contains an impurity for imparting electrical conductivity to said anode and cathode electrode materials.

15. An electrochemical treating method for electrochemically decomposing a substance contained in a gas or solution, which comprises introducing a gas or solution containing a substance to be treated into an electrolytic cell including a reaction chamber and an anode and a cathode spaced apart from said anode, said anode and cathode being arranged within the same reaction chamber, said anode including an electrode material made of diamond and said cathode including an electrode material made of diamond, passing an electric current through the electrolytic cell, and recovering a treated gas or solution.

16. The electrochemical treating method as claimed in claim 15, which comprises contacting a gas or solution containing a substance to be treated with said anode and cathode to decompose said substance into lower molecular weight components.

17. The electrochemical treating method as claimed in claim 15, which comprises contacting a gas or solution containing a substance to be treated with said anode and cathode so as to generate oxidizing and/or reducing species which in turn act to decompose said substance into lower molecular weight components.

18. An electrochemical treating method for electrochemically decomposing a substance contained in a gas or solution, which comprises introducing a gas or solution containing a substance to be treated into an electrolytic cell comprising an anode including an electrode material made of diamond, a cathode including an electrode material made of diamond and an ion exchange resin or an ion exchange membrane as an electrolyte disposed between said anode and said cathode, passing an electric current through the electrolytic cell, and recovering a treated gas or solution.

19. The electrochemical treating apparatus as claimed in claim 18, wherein said electrolyte comprises and ion exchange membrane and said anode and cathode are in close contact with opposing sides of said ion exchange membrane.

20. The electrochemical treating apparatus as claimed in claim 18, wherein said electrolyte comprises an ion exchange resin and said anode and cathode are in close contact with said ion exchange resin.

21. The electrochemical treating method as claimed in claim 18, which comprises contacting a gas or solution containing a substance to be treated with said anode and cathode to decompose said substance into lower molecular weight components.

22. The electrochemical treating method as claimed in claim 18, which comprises contacting a gas or solution containing a substance to be treated with said anode and cathode so as to generate oxidizing and/or reducing species which in turn act to decompose said substance into lower molecular weight components.

* * * * *